United States Patent [19]
Goble

[11] Patent Number: 5,411,523
[45] Date of Patent: May 2, 1995

[54] SUTURE ANCHOR AND DRIVER COMBINATION

[75] Inventor: E. Marlowe Goble, Logan, Utah

[73] Assignee: Mitek Surgical Products, Inc., Westwood, Mass.

[21] Appl. No.: 225,791

[22] Filed: Apr. 11, 1994

[51] Int. Cl.$^6$ .............................................. A61B 17/04
[52] U.S. Cl. ................................... 606/232; 606/104; 606/73; 81/471
[58] Field of Search ................ 606/104, 99, 86, 139, 606/148, 232, 72, 73; 81/121.1, 467, 471

[56] References Cited

U.S. PATENT DOCUMENTS

| | | | |
|---|---|---|---|
| 881,075 | 3/1908 | Hosking | 81/471 X |
| 985,087 | 2/1911 | Wilson | 81/121.1 |
| 3,894,467 | 7/1975 | Brescia | 411/352 |
| 4,184,915 | 1/1980 | Metcalf | 162/352 |
| 4,590,928 | 5/1986 | Hunt et al. | |
| 4,592,346 | 6/1986 | Jurgutis | |
| 4,632,100 | 12/1986 | Somers et al. | |
| 4,711,234 | 12/1987 | Vives et al. | |
| 4,738,255 | 4/1988 | Goble ert al. | |
| 4,779,616 | 10/1988 | Johnson | |
| 4,793,335 | 12/1988 | Frey et al. | |
| 4,946,468 | 8/1990 | Li | 606/232 |
| 4,960,420 | 10/1990 | Goble et al. | 606/72 |
| 4,988,351 | 1/1991 | Paulos et al. | 606/72 |
| 5,013,316 | 5/1991 | Goble et al. | 606/72 |
| 5,037,426 | 8/1991 | Goble et al. | 606/96 |
| 5,071,420 | 12/1990 | Paulos et al. | 606/99 |
| 5,100,417 | 3/1992 | Cerier et al. | 606/139 |
| 5,102,421 | 4/1992 | Anspach, Jr. | 606/232 |
| 5,139,520 | 8/1992 | Rosenberg | 623/13 |
| 5,207,679 | 5/1993 | Li | 606/72 |
| 5,211,650 | 5/1993 | Noda | 606/139 |
| 5,224,946 | 7/1993 | Hayhurst et al. | 606/72 |
| 5,236,445 | 8/1993 | Hayhurst et al. | 606/232 |
| 5,258,016 | 11/1993 | DiPoto et al. | 606/232 |

*Primary Examiner*—Tamara L. Graysay
*Attorney, Agent, or Firm*—M. Reid Russell

[57] ABSTRACT

A suture anchor and driver combination of the invention for use by a surgeon in a surgical procedure to secure a suture onto a bone surface for use in tying a ligament thereto. The anchor of the invention is preferably formed from a biodegradable polymer material, such as polylactic acid, polyglycotic acid, or other polymer ester, to be reabsorbed by the body after a ligament attached to the bone surface by the suture has experienced bone grown thereto. The anchor and driver are releasably secured together so as to allow the driver to be used to guide and position the anchor forward end into a hole that as been formed into a bone cortex. The anchor is preferably formed with wide spaced thread flights to provide a strong purchase when seated in the bone, with anchor turning provided by an appropriate turning of the driver, to seat the anchor in the bone hole. Whereafter the driver is arranged to be broken away from the anchor end and pulled therefrom leaving a suture extending from the anchor rear end.

8 Claims, 4 Drawing Sheets

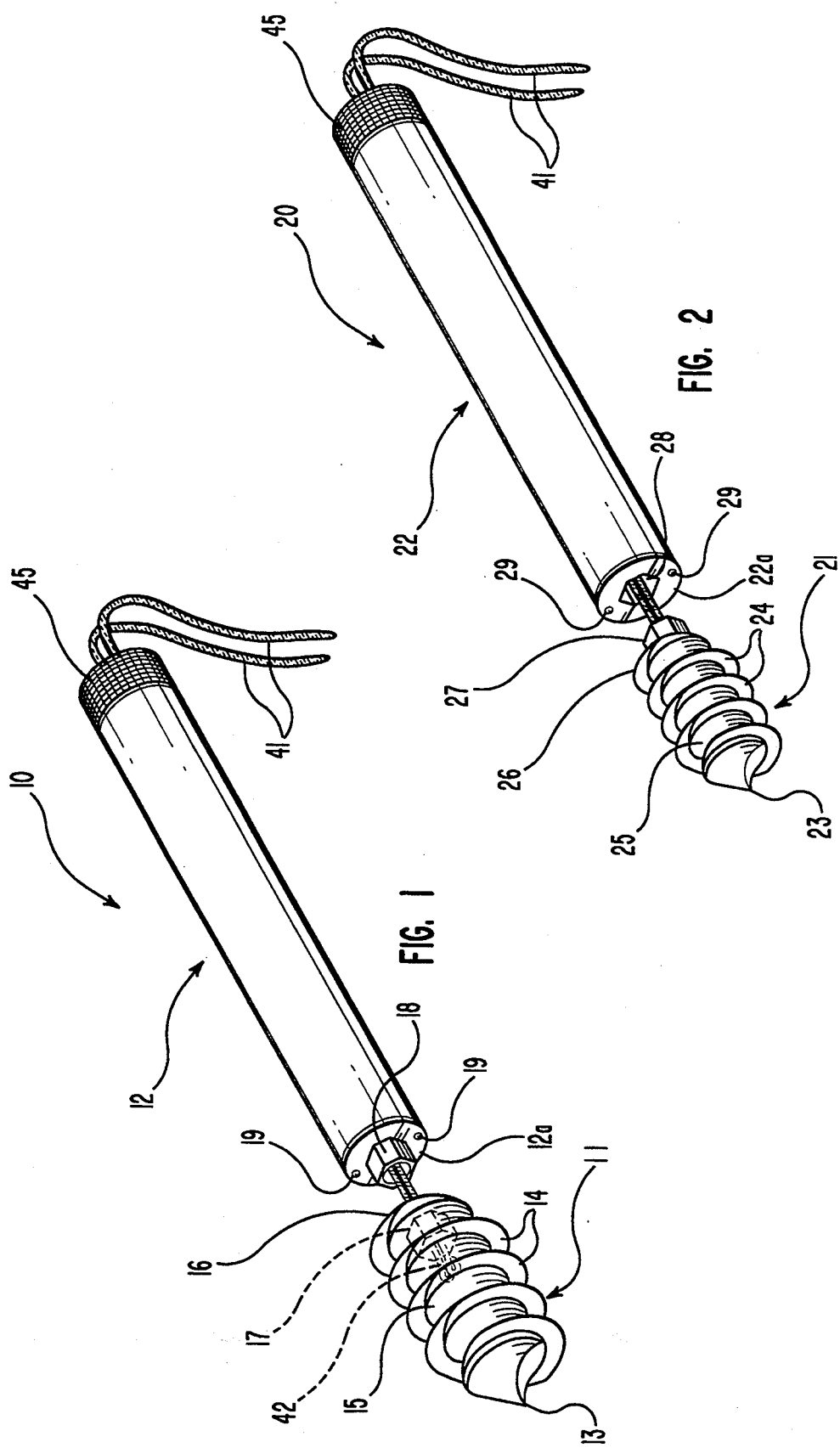

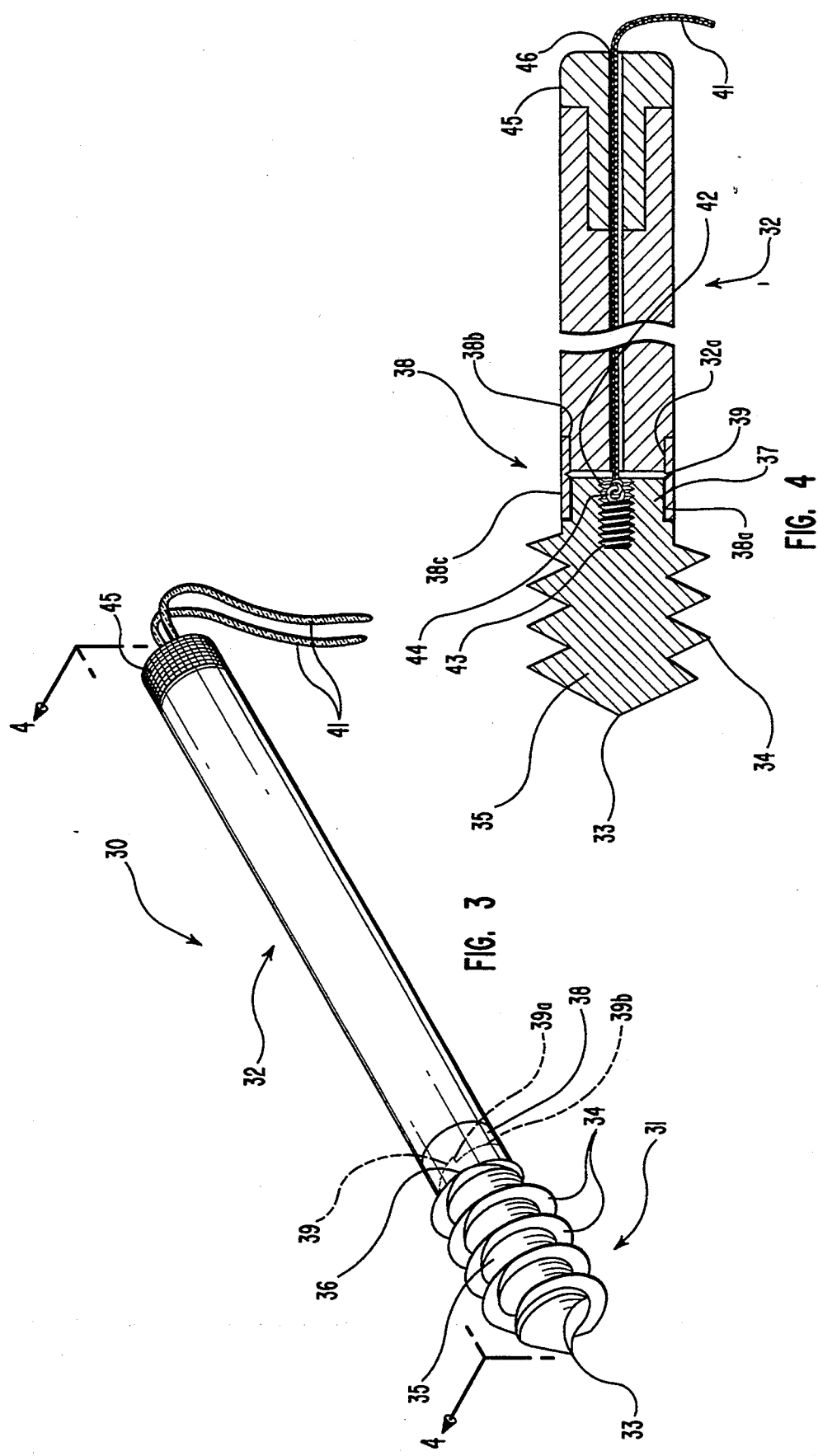

SUTURE ANCHOR AND DRIVER COMBINATION

BACKGROUND OF THE INVENTION

Field of the Invention

This invention relates to devices and arrangements of anchors for securing a ligament, or the like, to a bone surface during a ligament repair or replacement surgical procedure.

Prior Art

The present inventor is an inventor of earlier suture anchor devices and systems, set out in U.S. Pat. Nos. 4,632,100; 4,738,255; and 5,037,426. Additionally, the present inventor is an inventor of several inventions for clamping or tacking a ligament onto a bone surface, as set out in U.S. Pat. Nos. 4,960,420; and 5,013,316 and in a U.S. patent application in an Improved Channel Ligament Clamp, U.S. patent application Ser. No. 07/959,546. Similar to the cited suture anchor devices of the inventor, the present invention is in a device for turning an anchor into a bone mass, which anchor mounts a suture for use in securing a section of a ligament thereto. Unlike the earlier patents, the present invention is in an anchor that is constructed to provide for obtaining a strong bone purchase in a hole that has been formed into the bone surface for receiving the anchor. With anchor turning provided by a driver whose end is secured to the anchor end for turning and is arranged to be separated or broken off from the seated anchor, releasing the driver. The driver is then pulled away from the anchor, leaving a suture secured to and extending from the anchor rear end.

Additional to drivers shown in the cited patent to the inventor patents to others have been granted. None, however, have involved break-away anchor and driver combinations that is like that of the present invention.

Also, some examples of other devices for connecting ligament ends onto a bone surface or within a bone are shown in a patent to Hunt, et al., U.S. Pat. No. 4,590,928; and in patents that the present inventor is an inventor of, U.S. Pat. Nos. 4,632,100 and 4,738,255. Additionally, patents to Vives, et al., U.S. Pat. No. 4,711,234 and to Paulos, et al., U.S. Pat. No. 4,988,351, show, respectively, pin and disk couplings for providing for ligament mounting onto a bone surface. Additionally, devices for coupling a ligament onto a bone surface are shown in patents to Jurgutis, U.S. Pat. No. 4,592,346 and to Frey, et al., U.S. Pat. No. 4,793,335 that involve multi-pin staple arrangements.

None of the cited anchor and connector configurations, however, involve a combination anchor and driver arrangement where the driver, after turning the anchor into a hole that has been formed into a bone mass, can be easily and conveniently broken off from the anchor rear or coupling end and pulled therefrom, leaving a suture attached to which anchor end.

BRIEF SUMMARY OF THE INVENTION

It is a principal object of the present invention in a suture anchor and driver combination to provide a device for use for securing a suture to a bone cortex for attaching a ligament, or the like thereto.

Another object of the present invention is to provide an anchor turned by a connected driver into a hole that has been formed into the bone cortex, providing a strong purchase, whereafter the connected driver is broken off the anchor and removed, leaving a suture extending from the seated anchor.

Another object of the present invention is to provide a suture anchor and driver combination where the anchor includes wide spaced flights of threads to obtain a strong purchase.

Another object of the present invention is to provide a suture anchor and driver combination where the driver is attached to the anchor for guiding fitting of the anchor into and turning into a prepared hole formed into a bone mass and, with the anchor seated in which hole, the driver is arranged to be broken off from said anchor and removed, leaving a suture extending from which anchor exposed end.

Still another object of the present invention is to provide a suture anchor and driver combination where the anchor is formed from a biodegradable material that, after a period of time from implanting, will be reabsorbed.

Still another object of the present invention is to provide a suture anchor and driver combination where the anchor is easily installed into a pre-drilled and tapped hole that has been formed into a bone mass utilizing an attached driver, whereafter the driver is easily separated from the anchor and is pulled therefrom leaving a suture attached to the anchor for use for attaching a ligament onto the bone mass surface.

The suture and anchor combination of the present invention includes an anchor, that is preferably formed from a re-absorbable material, and is for implantation in a hole that has formed and tapped into a bone cortex. For providing a strong purchase the anchor is pointed at a forward end and is externally threaded to a rear end to have three to five flights wide and deep threads that are for turning into the hole that has been formed into the bone mass. A suture is attached to the anchor rear end and extends therefrom for use by a surgeon to attach a ligament, or the like, onto the bone surface. A driver, that is preferably a long shaft, is arranged with the anchor for mounting and turning it into the prepared hole, which driver forward end is arranged to be breakably secured to the anchor rear end.

The driver, with the anchor mounted to its forward end, is for use for guiding the anchor to and turning it anchor into the prepared hole to a depth where the anchor threads are fully seated in the bone, providing a strong purchase. In first and second embodiments of the invention the driver and anchor connection is a brittle adhesive bond that is broken by applying a bending force to the driver rear end and/or applying a tensile force to the driver to pull it off from the anchor. In another or third anchor and driver embodiment of the invention, ends of a driver and anchor are connected within a collar secured to the driver end that is scored around a collar mid-point in a stepped pattern. The scoring to provides opposing longitudinal surfaces in the direction of turning to seat the anchor into a hole formed into a bone with slopping surfaces in the opposite turning direction. The slopping surfaces are for separating from one another, along the scoring when the driver is turned in the opposite direction of turning. The suture, that is secured to the anchor rear end, is arranged for fitting into a longitudinal passage formed in the driver until the driver is pulled off of the seated anchor.

DESCRIPTION OF THE DRAWINGS

These and other objects and features of the present invention will become more fully apparent from the following description taken in conjunction with the accompanying drawings.

FIG. 1 is a side elevation perspective view of an embodiment of a first suture anchor and driver of the invention shown exploded apart;

FIG. 2 is a view like that of FIG. 1 showing another or second embodiment of the suture anchor and driver of the invention;

FIG. 3 is another view like that of FIGS. 1 and 2 showing still another or third embodiment of the suture anchor and driver of the invention;

FIG. 4 is a side elevation sectional view taken along the line 4—4 of FIG. 3 showing a driver end secured, by adhesive bonding, into one end of a connecting collar that is scored therearound with an anchor rear end shown fitted and secured as by an adhesive bonding into the opposite collar end, and showing a screw type mounting of a suture into the anchor rear end;

DETAILED DESCRIPTION

The invention is for use in an orthopedic surgical procedure, particularly to those involving techniques for attachment of a ligament onto a bone surface. In such procedure ligament attachment is greatly facilitated by securing a suture onto, to extend from, a bone surface whereto the ligament is to be attached, the suture for sewing a ligament thereto. After the ligament is in place, with a passage of time, the suture will be reabsorbed by the body. A preferred suture anchor of this invention is formed of a biodegradable material to also be reabsorbed by the body, with the patient's bone growth filling in the area where the anchor was installed. In practice, an anchor formed of a polymer such as titanium polylactic acid, polyglycotic acid or other polymer esters, with the driver formed from either a metal or polymer is preferred for use in the invention. Also non reabsorbable materials such as delvin or polyethylene can be used to form both the driver and anchor within the scope of this disclosure.

The anchor of the invention is required to provide a strong purchase that is resistive of being pulled out from a bone cortex after seating therein. Accordingly, the anchor is formed to have a plurality of flights of threads. In practice, an anchor having three to five flights has been used successfully, which threads are preferably wide for extending deep into the bone material so as to provide a strong purchase when turned therein. For providing which strong purchase, a cancellous thread has been found to provide a desired purchase when the anchor is properly seated in a hole that has been formed into a bone cortex. An anchor will vary depending upon size.

Figure 5:
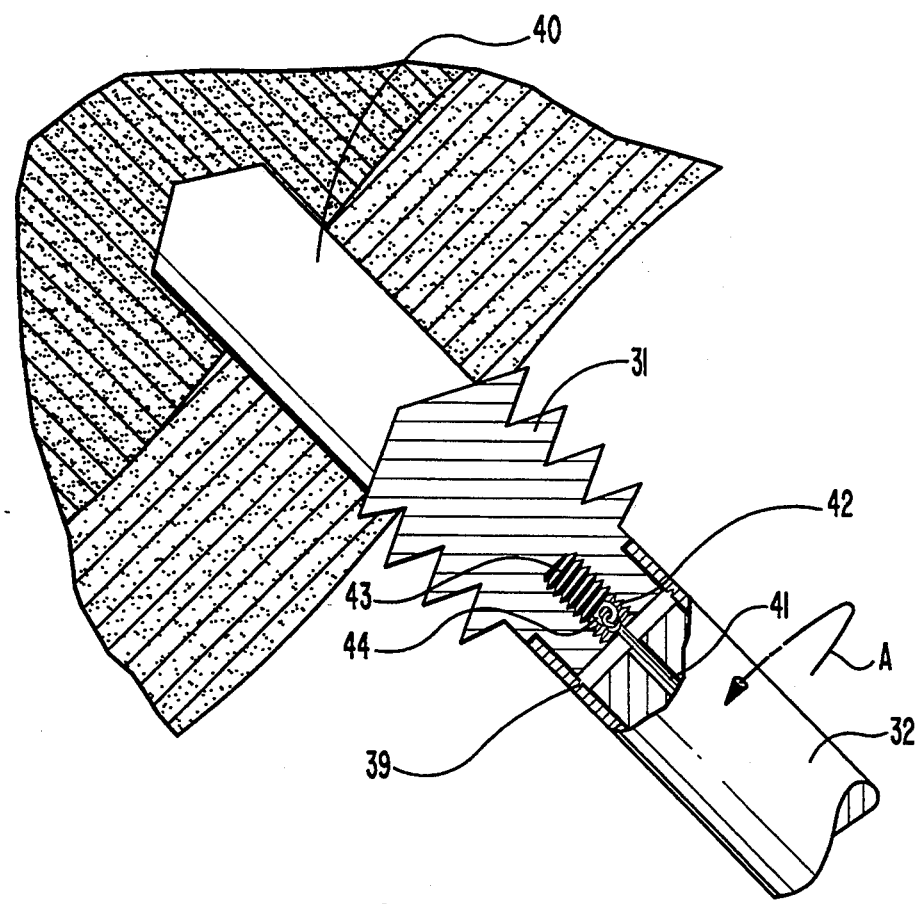
FIG. 5 is a side elevation view of the anchor and a forward end of the driver of FIGS. 3 and 4, showing the driver turning the anchor into a hole that has been formed into a bone endosteum.

The invention in a combination an anchor and driver and is illustrated in three embodiments shown in FIGS. 1, 2 and 3, identified, respectively, as anchor and driver 10 in FIG. 1, anchor and driver 20 in FIG. 2 and anchor and driver 30 in FIG. 3. Each anchor and driver combination 10, 20 and 30 includes, as shown, in FIG. 1, an individual anchor 11 and a driver 12; in FIG. 2, an individual anchor 21 and a driver 22; and in FIG. 3, an individual anchor 31 and driver 32. The exterior of each anchor 1, 21, and 31, respectively, is preferably identical, with each anchor and driver combination involving a different arrangement for releasably securing the anchor rear end onto the driver and includes similar arrangements for securing a suture into the anchor rear end. Each anchor 11, 21 and 31, is preferably formed from a reabsorbable material, as set out above, and though each preferably includes a pointed end 13, 23, and 33, respectively, the anchors are not generally suitable for turning directly into a bone cortex. Accordingly, as illustrated in FIG. 5, a hole 40 is preferably first drilled into the bone, that may be tapped, for receiving the anchor turned therein. Therefore, while the individual anchors are preferably pointed, they may be formed with flat forward ends. From around each anchor pointed end, a thread flight 14, 24, or 34 is shown extending along the anchor body 15, 25, and 35, to the anchor end 16, 26 and 36. FIGS. 1, 2 and 3 show the individual anchors as each including four (4) thread flights through, it should be understood, another number of thread flights, such as three or five flights, could be utilized within the scope of this disclosure. Which thread flights, as shown, are preferably wide to provide a large thread surface area for contact with bone material, as illustrated in FIGS. 5 through 8, so as to provide a strong purchase of the anchor within the bone making the anchor very resistive to being pulled out.

As shown in FIGS. 1, 2 and 3, the anchors 11, 21, and 31, each terminate in rear ends 16, 26, and 36, respectively. In FIG. 1, the anchor 11 end 16 is shown, in broken lines, as including an opening 17 that is sided, to have six (6) equal sides arranged as a hexagon. The sides of which opening 17 are for accommodating a like sided end extension 18 of driver 12 that extends, at a right angle outwardly, from the center of the driver 12 forward end 12a. The driver extension 18 seats in opening 17, such that the extension sides are in engagement with the sides of the anchor 11 opening. Shown in FIG. 5, turning of the driver turns also the anchor to where the anchor thread flights will engage and enter the bone material surrounding hole 40, seating therein. Such turning is provided by turning the driver in a clockwise direction, as illustrated by arrow A.

Figure 7:
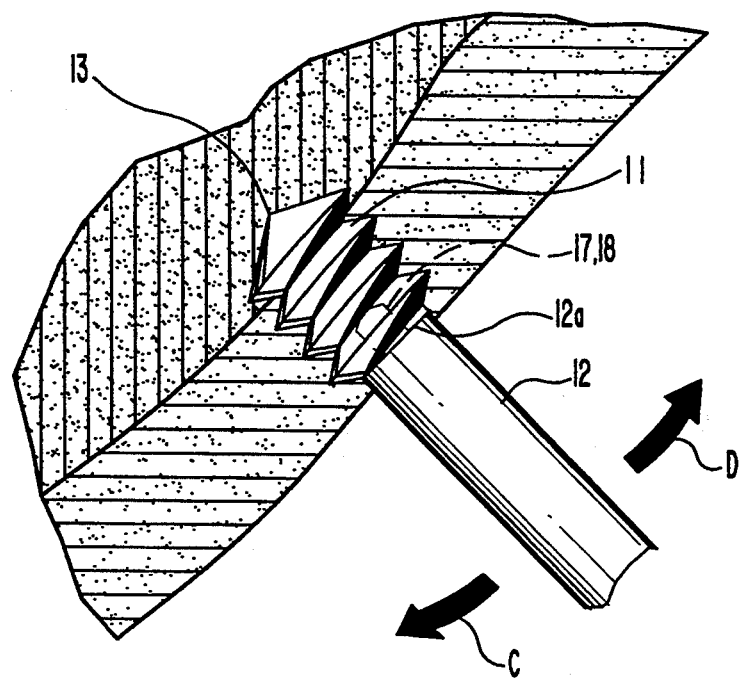
FIG. 7 is a view like FIG. 6 except the driver and anchor of FIG. 1 have been substituted for the driver and anchor of FIG. 3, and showing, with arrows the driver being rocked back and forth across the anchor end to break an adhesive bead coupling of the anchor onto the driver end.

The invention provides for connecting the anchor 11 and driver 12 together whereby the driver is used for both directing the anchor to a hole 40, that has been formed into a bone cortex, and for turning the anchor into that hole, as shown in FIG. 5, turning to continue until the anchor is fully seated in hole 40, as illustrated in FIG. 7. Whereat, the driver 12 is separated from the anchor 11 and pulled therefrom leaving a suture 41 extending from the anchor rear end.

For providing a frangible connection between the anchor and driver end 12a, beads of a brittle adhesive 19, such as cyanoacrylate, are applied between the anchor and driver surfaces. An adhesive bonding is thereby provided that will be sufficient to allow the driver to be used to guide the anchor to hole 40 and for turning it therein. Which adhesive bonding, however, can be broken by bending the driver 12 back and forth across the anchor rear end, as illustrated by arrows C and D in FIG. 7, and/or by applying a tensile force to the driver so as to pull it off from the anchor end, breaking the adhesive bond.

The anchor and driver combination 20 of FIG. 2 is essentially like that of FIG. 1, except that it includes a sided center opening 28 that has been formed into the driver end 22a, that is preferably six sided to have a hexagonal cross section, and is to receive a like sided anchor rear end extension 27. In this arrangement, the extension 27 projects from the anchor 11 rear face 26 and the sided opening 28 is formed in the driver forward end 22a. Like the arrangement of FIG. 1, the anchor 21 and driver 2 of FIG. 2 are preferably maintained together by an application of one or more beads of a brittle adhesive 29, such as cyanoacrylate, therebetween. So arranged, after the driver is used for positioning and turning the anchor 21 into hole 40, it is separated from the anchor, as by bending it back and forth, illustrated by arrows C and D in FIG. 7, separating the driver form the anchor, as described hereinabove.

Figure 6:
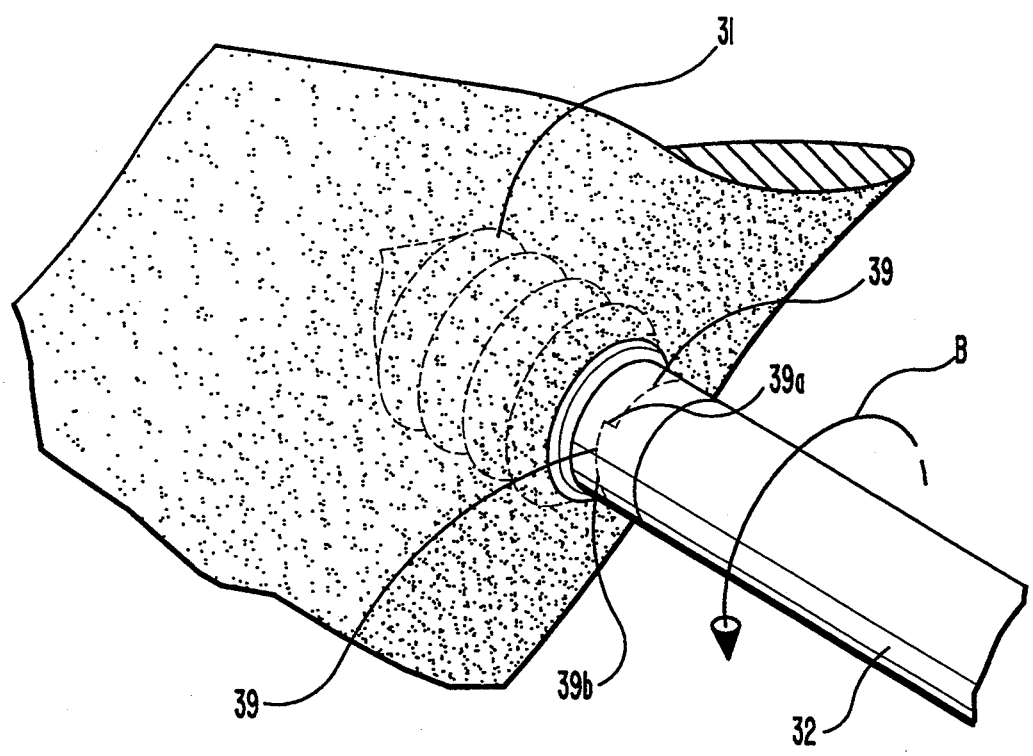
FIG. 6 is a view like FIG. 5 only showing anchor, in broken lines, seated in the bone cortex hole and showing the driver direction of turning as reversed to break the scoring between the driver end and anchor to release the driver.
Figure 8:
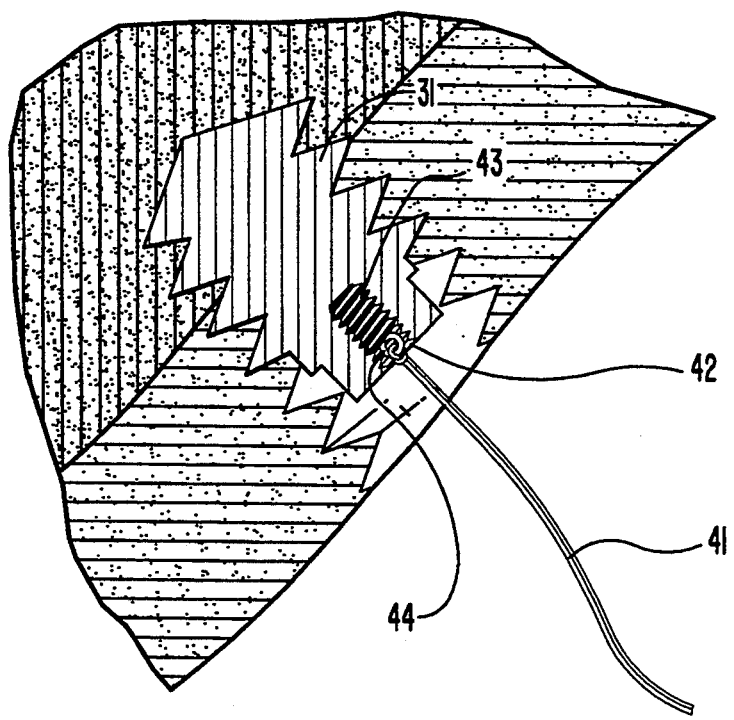
FIG. 8 shows a seated anchor after a driver has been removed, releasing a suture that is shown extending from the anchor end.

FIG. 3 shows anchor 31 and driver 32 of the invention that are connected together by a frangible collar 38. The collar 38, on a forward end 38a, telescopes over a cylindrical rear end 37 of anchor 31. FIG. 3 shows the other or opposite collar end 38b telescoped over a cylindrical forward end 32a of driver 32. The respective telescoped couplings are bonded together, preferably by application of an adhesive therebetween, by heat bonding, or the like, f \to form a permanent welding together of the opposing surfaces. The frangible collar 38, as shown best in FIGS. 3 and 6, is preferably scored at 39, as shown in broken lines, around a center section 38c. Which scoring 39 has a lightening bolt appearance with, as shown in broken lines, spaced apart longitudinal segments 39a that are connected at their respective opposite ends by sloping lines 39b. So arranged, the anchor 31 is secured to the driver 32 forward end for alignment with a hole 40 formed into a bone cortex, as illustrated in FIG. 5. Once positioned, a clockwise turning force applied to the driver 32, illustrated by Arrow A, will be transferred through the opposing sides of the collar longitudinal segments 39a and into the anchor 31. The anchor is thereby turned into hole 40 to where it is fully seated thereon, as illustrated by the broken line representation of anchor 31 in FIG. 6. Thereafter, reversing the direction of driver 32 turning, illustrated as Arrow B, will apply a force to separate the collar longitudinal segments 39a. The collar is preferably separated along the sides of the collar sloping lines 39b separating the collar 38 into two sections. The collar 38 is thereby broken apart to allow the driver 32 to be pulled off of the anchor 31, exposing, as shown in FIG. 8, the suture 41 that is connected to and extends from the anchor rear end.

The suture 41, as set out above can be secured into the anchor 11, as illustrated in FIG. 1, at a suture bend, shown in broken lines, and fitted into a longitudinal center hole 42 formed in the top of anchor end 16 cavity 17, and fitting a screw, wedge, or the like, not shown, or applying an adhesive therein, to bind the suture 41 bend or bends in which center longitudinal hole 42. Alternatively, as shown in FIGS. 4, 5, and 8, the anchor 31 and 37 is drilled with center longitudinal hole 42 that is then tapped to receive a set screw 43, or the like, turned therein that includes a ring 44 formed into to and extend from its rear end whereto the suture 41 is shown tied. The set screw 43 and ring 44, like the anchor 31, are preferably formed form a material such as a polymer material such as polylactic acid, polyglycotic acid, or other polymer esters, or the like, that will be reabsorbed by the body during the healing process.

While above set out suture mounts are preferred for the described anchors, it should be understood, that other arrangements can be used on the described anchors, within the scope of this disclosure without departing from the subject matter contained herein.

To accommodate the suture 41 therein each driver 12, 22, and 32 is preferably open longitudinally. Which opening is preferably covered at a top end by a cap 45, or the like that has a center longitudinally opening 46 to receive the suture 41 threaded therethrough. The cap 45 may be formed for striking, as with a hammer, for transmitting a hammer blow through the driver and into the anchor for initially seating it in hole 40, as shown in FIG. 5. Whereafter, the driver is used to turn the anchor so as to fully seat it, as shown in FIGS. 6, 7, and 8, in the hole 40.

After anchor seating, the driver is separated off from the anchor rear end. FIG. 6 shows at Arrow B, the driver 32 being turned opposite to its direction of turning Arrow A, to seat the anchor 11, shown as counter clockwise to break frangible collar 38 along scoring 39. In FIG. 7, the driver 12, that should be taken as being driver 22 also, is shown being pivoted back and forth across and pulled away from the anchor all and 16. This action is taken to separate the driver 12 extension 18 out from the anchor opening 17, breaking the driver off from the anchor that is then pulled therefrom to expose suture 41.

The anchors 11, 21, and 31 each mount suture 41 such that, when fully seated in the hole 40, the suture 41 will extend from the seated anchor rear end to attach, as by tying, sewing, or the like, a ligament, or the like, onto the bone surface, not shown.

While preferred embodiments of my invention in a suture anchor and driver combination have been shown and described herein, it should be understood that the present disclosure is made by way of example only and that variations to the invention and its utilization are possible within the scope of this disclosure without departing from the subject matter coming within the scope of the following claims, and a reasonable equivalency thereof, which claims I regard as my invention.

I claim:

1. A suture anchor and driver combination comprising, a driver that includes a suture anchor coupling means on a forward end thereof and is open longitudinally therethrough; a suture anchor having a driver coupling means with a means for mounting said suture anchor in a hole that has been formed into a bone cortex, and said suture anchor includes means for mounting a suture to extend from a rear end thereof; and a frangible means for joining said driver and said suture anchor at their respective coupling means that can be broken by application of a force to said driver.

2. A suture anchor and driver combination as recited in claim 1, wherein the suture anchor is formed from a material that is suitable for human implantation.

3. A suture anchor and driver combination as recited in claim 2, wherein the suture anchor is formed from titanium.

4. A suture anchor and driver combination as recited in claim 2, wherein the suture anchor is formed from a polymer material that is reabsorbed by the body.

5. A suture anchor and driver combination as recited in claim 1, wherein the frangible means is a bead of a brittle adhesive applied between the driver forward end and the suture anchor rear end.

6. A suture anchor and driver combination as recited in claim 1, wherein the frangible means is a frangible collar that is open therethrough for disposition between by fitting over the suture anchor rear end and the driver forward end, respectively, which said collar is formed to shear therearound, breaking apart when the driver is turned appropriately.

7. A suture anchor and driver combination as recited in claim 6 wherein the frangible collar, to break apart, is scored centrally therearound as a series of a sloping section portions that each end in a segment that is parallel to the collar longitudinal axis, said collar scoring parallel segments for transforming a force of driver turning into the suture anchor to turn it into the bone cortex hole and said sloping portion of said scoring to separate when said driver is turned in the opposite turning direction.

8. A suture anchor and driver combination as recited in claim 6, wherein the frangible collar is formed from a plastic material.

* * * * *